United States Patent [19]
Schweitzer et al.

[11] Patent Number: 5,739,442
[45] Date of Patent: Apr. 14, 1998

[54] METHOD FOR MONITORING CONDITIONS OF OBJECTS INCLUDING EDGE DETECTING AND TRAVEL DIRECTION REVERSING STEPS

[75] Inventors: David Paul Schweitzer, North Canton; James Arthur Grimes, Sr., Akron, both of Ohio

[73] Assignee: The Goodyear Tire & Rubber Company, Akron, Ohio

[21] Appl. No.: 787,480

[22] Filed: Jan. 21, 1997

Related U.S. Application Data

[62] Division of Ser. No. 536,504, Sep. 28, 1995, Pat. No. 5,618,999.

[51] Int. Cl.[6] .................................................. G01M 19/00
[52] U.S. Cl. ............................................................ 73/866.5
[58] Field of Search .................................. 73/866.5, 1 R, 73/104, 865.8, 865.9, 146, 1 J, 1 D, 1 DV, 635–641, 1.01, 1.79; 324/202, 220, 221; 198/810.01, 810.02, 810.03; 33/711, 744, 745, 776

[56] References Cited

U.S. PATENT DOCUMENTS

| | | | |
|---|---|---|---|
| 3,371,524 | 3/1968 | Wloszek | 73/1 DV X |
| 3,731,113 | 5/1973 | Lowe et al. | 307/119 |
| 3,742,477 | 6/1973 | Enabnit | 340/259 |
| 3,834,524 | 9/1974 | Ratz et al. | 198/232 |
| 3,939,570 | 2/1976 | Loftus | 33/544.3 |
| 3,952,581 | 4/1976 | Gottelt | 73/640 |
| 3,956,632 | 5/1976 | Hall et al. | 198/812.03 X |
| 4,194,149 | 3/1980 | Holt et al. | 324/220 |
| 4,285,243 | 8/1981 | Collingwood | 73/623 |
| 4,312,230 | 1/1982 | Bricker et al. | 73/638 |
| 4,441,727 | 4/1984 | Durcan | 280/62 |
| 4,462,523 | 7/1984 | Kerr | 198/810 |
| 4,468,620 | 8/1984 | Vaerman | 73/866.5 X |
| 4,621,727 | 11/1986 | Strader | 198/810 |
| 4,628,454 | 12/1986 | Ito | 364/424.059 |
| 4,722,001 | 1/1988 | Röhrich et al. | 324/220 X |
| 4,747,317 | 5/1988 | Lara | 73/865.8 |
| 4,757,258 | 7/1988 | Kelly, Jr. et al. | 324/220 |
| 4,854,446 | 8/1989 | Strader | 198/810 |
| 4,878,554 | 11/1989 | Dion | 180/19.3 |
| 4,886,478 | 12/1989 | Jones | 446/176 |
| 5,101,920 | 4/1992 | Peterson | 180/11 |
| 5,133,220 | 7/1992 | Alford et al. | 73/866.5 |
| 5,370,006 | 12/1994 | Zollinger et al. | 73/865.8 |
| 5,473,953 | 12/1995 | Appel | 73/866.5 |

FOREIGN PATENT DOCUMENTS

| | | | |
|---|---|---|---|
| 4-106016 | 4/1992 | Japan | B65G 43/02 |
| 6-24538 | 2/1994 | Japan | B65G 43/02 |
| 6-58850 | 3/1994 | Japan | G01M 19/00 |

OTHER PUBLICATIONS

Article entitled Magnetic Sensor NDE for Quality Control in Manufacture of Steel Based Products. 5 pages published 5, Apr. 1997.

Manual entitled "Hall Probe Steel Cord Detector Technical Manual CSIRO", Jun. 1989. 19 pages.

*Primary Examiner*—Thomas P. Noland
*Attorney, Agent, or Firm*—Roger D. Emerson

[57] ABSTRACT

An apparatus and method for monitoring the condition at or near the surface of objects is disclosed. The apparatus is a vehicle which includes a housing which is supported and translated across the object surface by three wheels. The front or first wheel is associated with an encoder and sensor which magnetically determines the physical condition of the object. The apparatus includes a starter block which includes a series of metallic wires embedded at certain depths and locations within the starter block. The vehicle passes over the starter block prior to passing over the object in order that the vehicle be recalibrated by the starter block prior to observing the physical condition of the object.

11 Claims, 6 Drawing Sheets

METHOD FOR MONITORING CONDITIONS OF OBJECTS INCLUDING EDGE DETECTING AND TRAVEL DIRECTION REVERSING STEPS

This is a division of application Ser. No. 08/536,504, filed Sep. 28, 1995 and now U.S. Pat. No. 5,618,999.

BACKGROUND OF THE INVENTION

This invention pertains to the art of methods and apparatus for monitoring the physical condition of an object. One application of the invention is articles incorporating metallic members, such as conveyor belts which are reinforced with cabled wires.

The present invention contemplates a new and improved method and apparatus for monitoring the condition of products reinforced with metallic reinforcements, such as conveyor belts reinforced with steel cables.

SUMMARY OF THE INVENTION

In accordance with the present invention, a new and improved method and apparatus for monitoring the condition of an object is provided.

More particularly, in accordance with one aspect of the invention, an apparatus for monitoring the condition of an associated article reinforced with metallic cords includes a vehicle having a housing having an interior and a bottom. The apparatus includes locomotion means for locomoting the vehicle across the associated article. The locomotion means are affixed to the bottom of the housing. The interior of the housing includes sensing means for sensing metallic cords in the associated article.

In accordance with another aspect of the invention, the apparatus includes an encoder means for measuring translational distance traveled by the apparatus.

According to another aspect of the invention, the apparatus includes a sensor which is associated with the encoder means and which is mounted inside a first wheel which is mounted on the housing.

According to another aspect of the invention, the apparatus includes a starting block which has several metallic members mounted therewithin. The housing selectively passes over the starting block before passing over the associated article, thereby the sensing means senses the first metallic member, and then other metallic members, in the starting block and is recalibrated before translating over the associated article.

According to another aspect of the invention, an apparatus for recalibrating an associated monitoring means from monitoring the location and condition of metallic cords in an associated article. The apparatus includes a body which has a top surface and a bottom surface and a thickness therebetween and a first metallic member mounted within the body. The first metallic member comprises a wire or cable. The apparatus further includes second, third, fourth and fifth metallic members, all mounted at specific locations different from the others.

According to a still further aspect of the invention, a method for monitoring the location and condition of metallic members within an associated article includes the steps of traversing a width of the associated article with a vehicle, sensing the location and condition of the metallic members in the associated article while the vehicle traverses the width of the associated article identifying an edge of the associated article, and stopping the vehicle at the edge of the associated article.

According to a further aspect of the invention, the method includes the step of calibrating the vehicle prior to traversing the width of the associated article, by traversing the vehicle over a starting block having metallic members embedded therewithin.

One advantage of the present invention is the provision of a new apparatus which can monitor the location and condition of metallic members within an article, such as the condition and location of metallic reinforcements within a conveyor belt.

Another advantage of the present invention is its automated nature, being able to recalibrate itself, travel the width of a conveyor belt gathering data, and return to a convenient location for the operator to pick up and move the apparatus to the next desired location.

Another advantage of the present invention is its portability, so that such apparatus is easily carried to and used at remote locations. Since one of the primary objects of the invention is the monitoring of conveyor belts, and since conveyor belts are often used at locations difficult to reach, the portability of the invention is a primary benefit.

Another advantage of the invention is the recalibration of the apparatus before every traversing of the belt. Such constant and systematic recalibration prevents "drift" and ensures accurate data. Still other benefits and advantages of the invention will become apparent to those skilled in the art to which it pertains upon a reading and understanding of the following detailed specification.

BRIEF DESCRIPTION OF THE DRAWINGS

The invention may take physical form in certain parts and arrangements of parts, a preferred embodiment of which will be described in detail in this specification and which will be illustrated in the accompanying drawings, which form a part hereof and wherein.

DESCRIPTION OF THE PREFERRED EMBODIMENT

Figure 1:
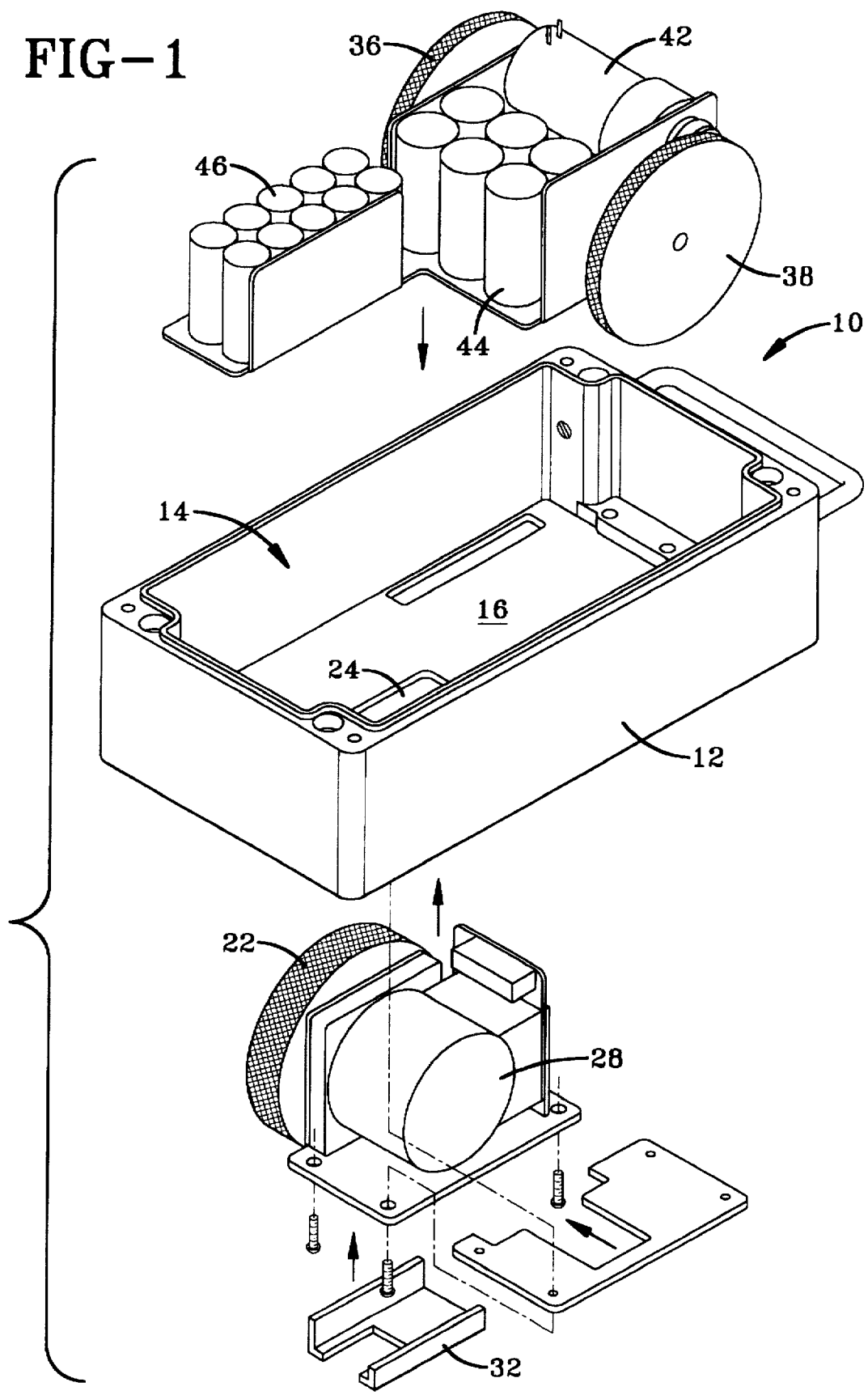
FIG. 1 is an exploded view of a vehicle according to the invention.
Figure 2:
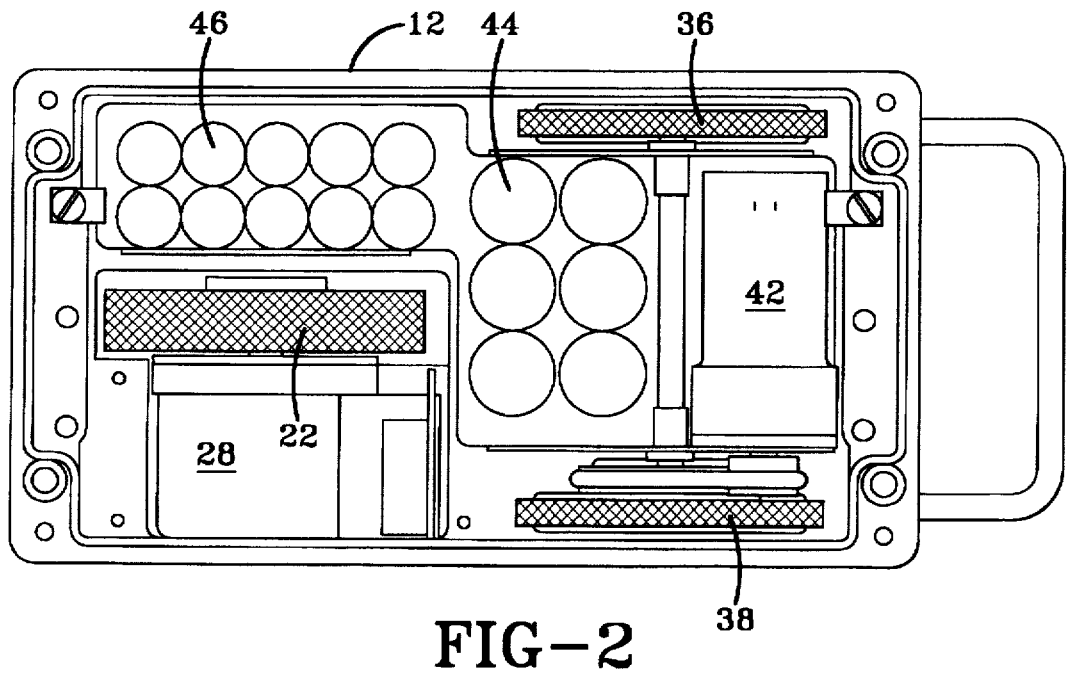
FIG. 2 is a top cross-sectional view of a vehicle according to the invention.
Figure 3:
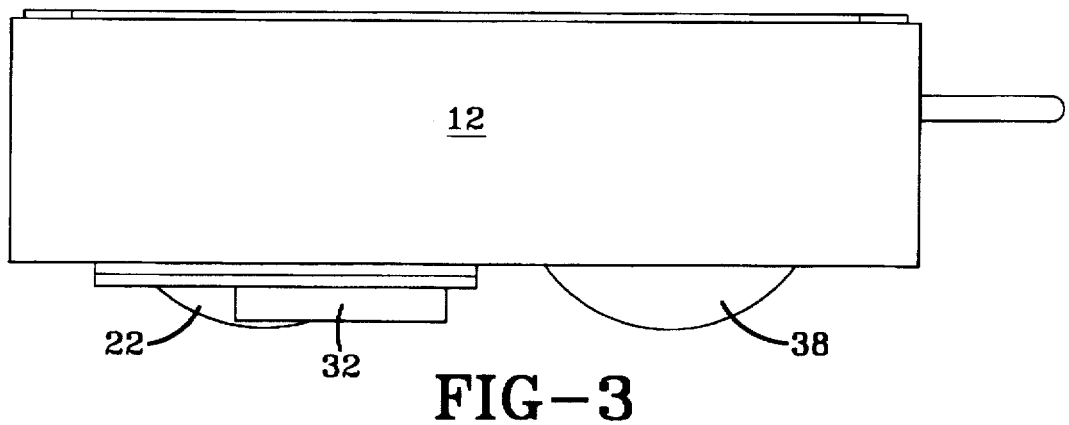
FIG. 3 is a side view of the vehicle shown in FIG. 2.
Figure 4:
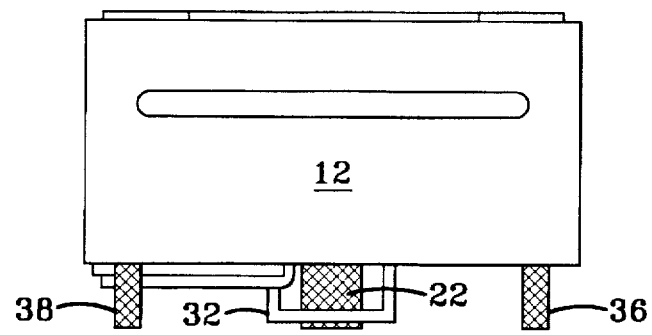
FIG. 4 is a rear view of the vehicle.

Referring now to the drawings wherein the showings are for purposes of illustrating a preferred embodiment of the invention only and not for purposes of limiting the same, FIG. 1 shows an exploded view of the primary components of a vehicle 10 according to the invention. The vehicle 10 includes a housing 12 which includes an interior 14 and a bottom surface 16. A front or first wheel 22 fits through a slot 24 in the bottom surface 16 of the housing 12. The first wheel 22 is made of aluminum and is operatively associated with and connected to encoder means 28.

With reference to FIGS. 1–6 and 9, the encoder means 28 measures the distance the vehicle 10 travels across the width 78 of an associated conveyor belt 80. The first wheel 22 is also associated with a slide shoe 32, the operation of which will be discussed later. A sensor 62 is associated with the encoder means 28 and is mounted within the first wheel 22. The sensor 62 in the preferred embodiment is an Allegro microsystems model UGN3503 linear Hall effect sensor. For this application, the sensor 62 is magnetically driven with an Alnico-5 permanent magnet 94 which is 0.25 inches in diameter by 0.75 inches in length. While the preferred sensor 62 operates via the Hall effect, other physical characteristics and phenomena can be utilized to gather the desired information. The sensor 62 is epoxied to the end of the magnet 94. The encoder means 28 is mounted on an encoder shaft 30. The magnet 94 is mounted on a magnet\sensor mount 54.

While different sensors will work, the preferred sensor 62 is a Hall effect type sensor. As the sensor 62 senses the steel cables 81,82,83,84,85 in the starter block 70, the steel cables 81,82,83,84,85 which are closer to the axis of the magnet 94 increases the magnetic field coupling. This increased magnetic field coupling is sensed by the linear Hall effect sensor 62 and can be translated into the data desired. The centerline of the individual metallic cable 81,82,83,84,85 in question is at the peak of the signal. The horizontal position of the cable 81,82,83,84,85 is measured by the encoder when the peak occurs and is saved as the horizontal position of the cable. The amplitude of the signal at the peak is the depth of the cable 81,82,83,84,85 within the starter block 70.

One advantage of the encoder means 28 being connected to the front wheel 22 of the vehicle 10 is that the sensor 62 is positioned at the centerline of the vehicle 10 and inside the front wheel 22. By mounting the encoder means 28 and sensor 62 in this way, the magnetic field reaches through the aluminum front wheel and into the conveyor belt. The sensor 62 is not subject to mechanical abuse since it is mounted inside the first wheel 22 and close tracking is assured since the sensor 62 is just above the contact point of the front wheel 22.

With reference to FIGS. 1–6, also mounted within the interior 14 of the housing 12 are second and third wheels 36,38. Second and third wheels 36,38 are attached to a motor 42 which is powered by battery 44. Together with the second and third wheel 36,38, the motor 42 provides the locomotive means for translating the vehicle 10 across the width of a conveyor belt.

Figure 5:
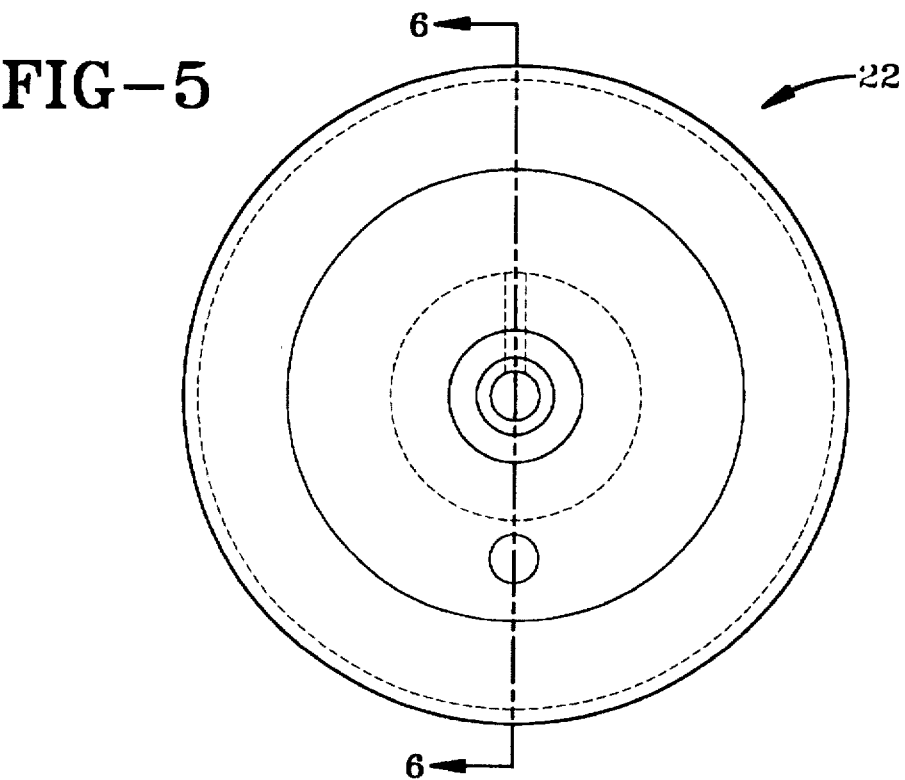
FIG. 5 is a side view of a front or first wheel of the invention.
Figure 6:
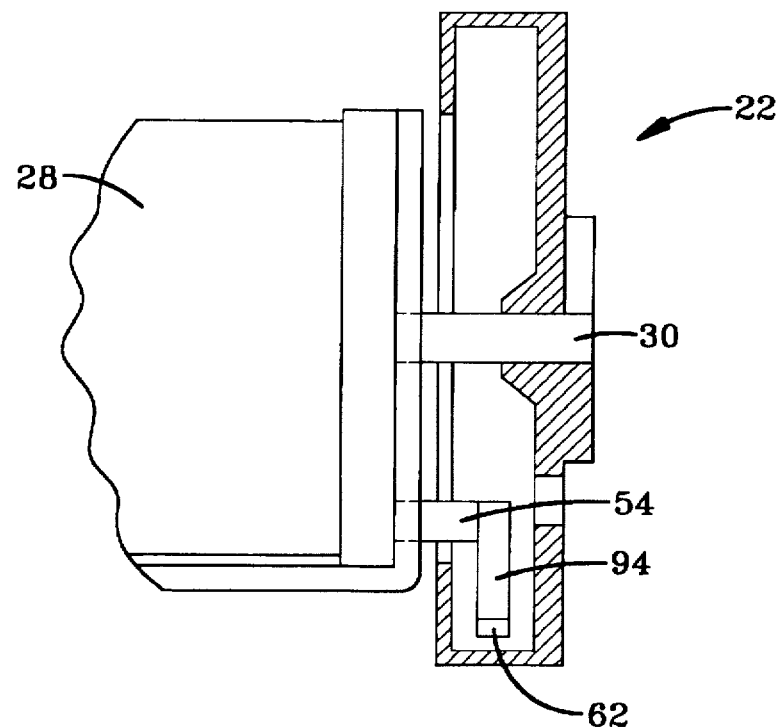
FIG. 6 is a cross-sectional view of the front or first wheel of the invention taken along line 6—6 of FIG. 5.

With reference to FIGS. 5 and 6, the first wheel 22 will be further discussed. First wheel 22 is essentially "C-shaped" in cross section and partially encloses an interior. Sensor 62 is located in the interior of first wheel 22 just above the contact point of the first wheel 22. While first wheel 22 rotates on encoder shaft 30, the sensor 62 remains in a fixed position above the contact point of the first wheel 22. In the preferred embodiment, the first wheel 22 is made of aluminum and has a 3 inch diameter and a width of about 0.63 inches.

Figure 7:
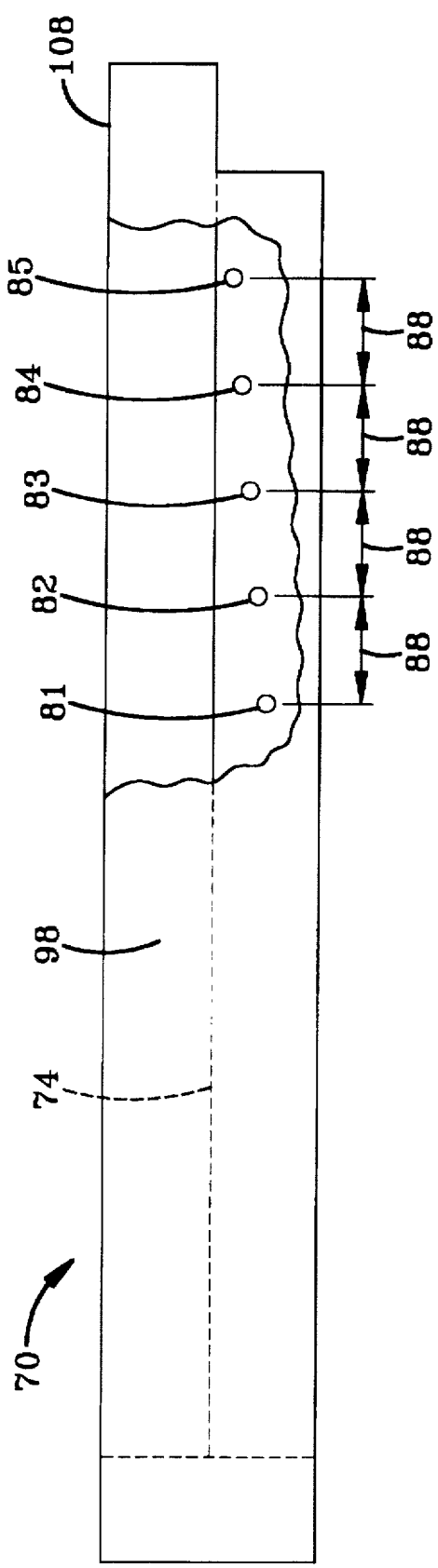
FIG. 7 is a side view of a starting block according to one aspect of the invention.
Figure 8:
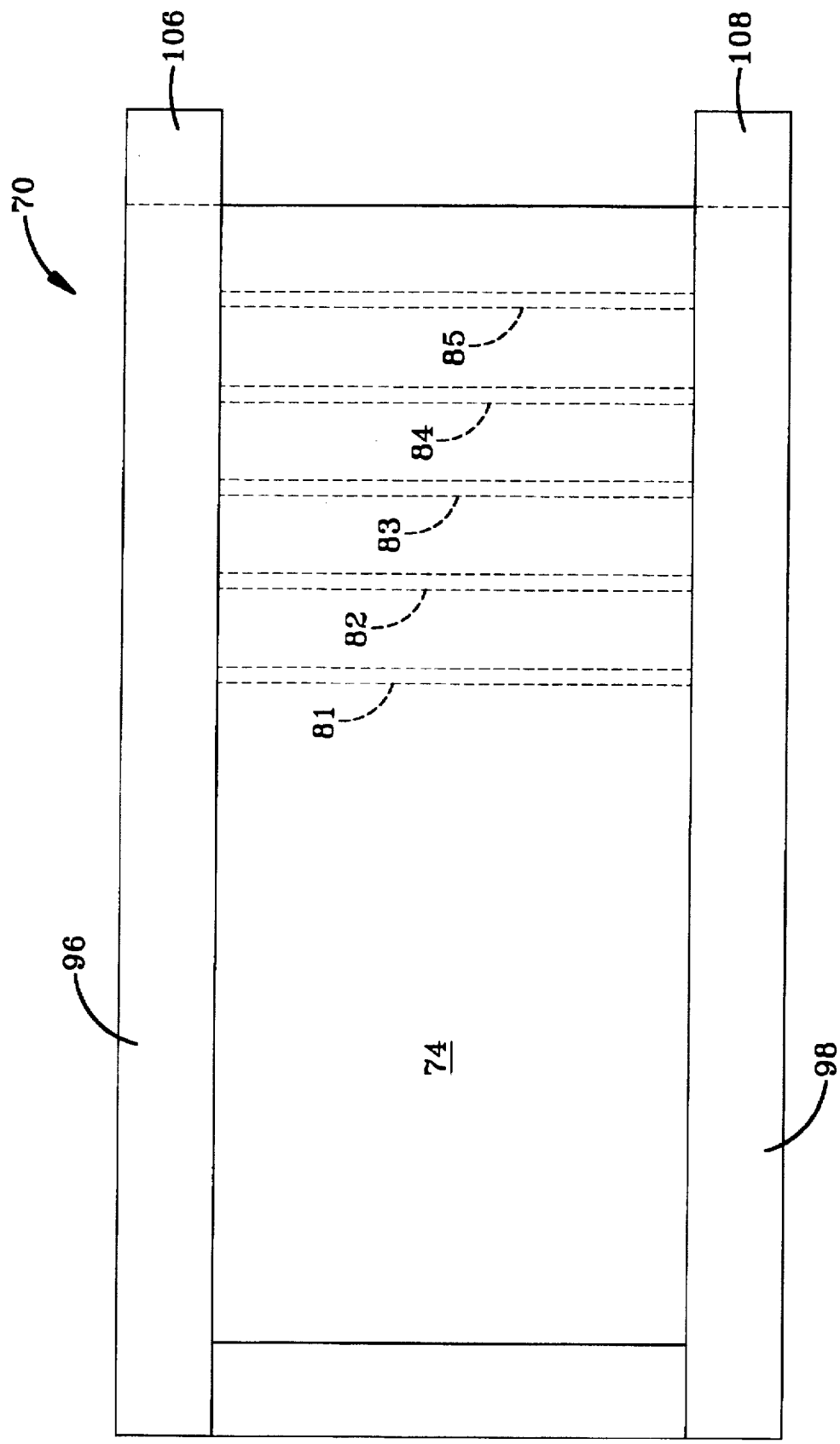
Fig. 8 is a top view of the starting block of FIG. 7.

With reference to FIGS. 7 and 8, another aspect of the invention will be described. A starter block 70 has a generally rectangular configuration. It is preferably made of elastomer, such as rubber. Its most distinguishing features are five wires embedded therein and their respective locations. First, second, third, fourth, and fifth wires 81,82,83, 84,85, are mounted within the starter block 70 and, as can be seen with reference to FIGS. 7 and 8, are separated by a fixed distance 88 along the width of the starter block 70. In the preferred embodiment, the fixed distance 88 is about 1 inch. With reference to FIG. 7, it can be seen that the wires 81,82,83,84,85 are also separated in the vertical dimension, meaning the respective wires 81,82,83,84,85 are embedded in the starter block 70 at different heights. As can be seen by reference to FIG. 7, the first wire 81 is lower than the other wires and the wires 81,82,83,84,85 are arranged in a "stair step" configuration.

By arranging the wires 81,82,83,84,85 in such a manner, the vehicle 10 can be recalibrated by simply passing it over a working surface 74 of the starter block 70. Because the wires 81,82,83,84,85 are placed in the starter block 70 at known locations, the data can be fed to the vehicle 10, allowing it to be recalibrated prior to measuring the actual article in question, such as a conveyor belt 80.

Figure 9:
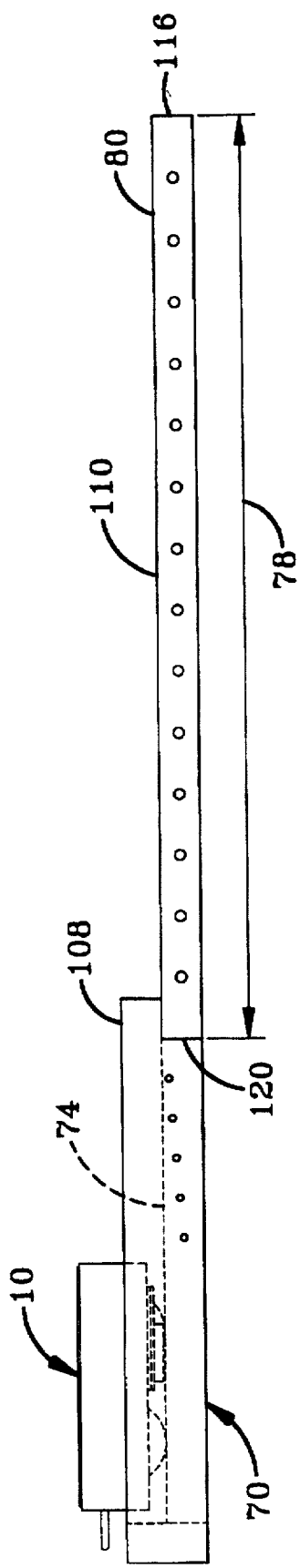
FIG. 9 is a schematic, cross-sectional view of the apparatus according to the invention.

With continuing reference to FIGS. 7–9, the starter block 70 further includes a working surface 74 which is bounded by first and second walls 96,98 respectively. The first and second walls 96,98 extend slightly above the plane of the working surface 74 to help guide the vehicle 10 forward onto the associated conveyor belt 80. One end of each of the walls 96,98 terminates in ears 106,108. The ears 106,108 fit over the top surface of the conveyor belt 80 so the working surface 74 of the starting block 70 is at essentially the same plane as the top surface of the conveyor belt 80.

The vehicle 10 disclosed above, when used in association with the starter block 70, provides a new method of monitoring the location and condition of metallic members within an associated article, such as the location and condition of metallic cords within a conveyor belt 80. The inventive method includes the steps of calibrating the vehicle 10 prior to traversing a width 78 of the associated article 80, with the calibration being accomplished by traversing the vehicle 10 over the starting block 70. Next the vehicle 10 traverses the width of the associated article, such as the conveyor belt 80. While doing so, the vehicle 10 rolls on first, second, and third wheels 22,36,38 until the first wheel 22 rolls off an edge 116 of the conveyor belt 80. By doing so, the edge 116 of the conveyor belt 80 is identified and the vehicle 10 stops progressing forward. When the first wheel 22 of the vehicle 10 rolls off the edge 116 of the conveyor belt 80, its speed goes to zero. A sealed bearing in the encoder means 28 does not permit the first or front wheel 22 to coast. When the speed of the first wheel 22 goes to zero, this event is detected by the encoder means 28. The computer is programmed to reverse the direction of the motor 42 upon such occurrence and the vehicle 10 progresses backward across the conveyor belt 80 a preset distance. The vehicle 10 traverses the conveyor belt 80 a second time in the reverse direction a distance shorter than the distance it traveled forward across the same conveyor belt 80. The return trip is shorter so that the vehicle 10 does not leave the other edge 120 of the conveyor belt 80 and again enter the starter block 70, but instead remains on the top surface 110 of the conveyor belt 80 at a location convenient for the operator.

When the first wheel 22 of the vehicle 10 rolls off the edge 116 of the conveyor belt 80, the slide shoe 32 prevents the vehicle 10 from tipping over.

The invention has been described with reference to a preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is now claimed:

1. A method of observing a physical condition of an object at or near a surface of the object, the object having opposed lateral first and second edges, the method comprising the steps of:

causing a vehicle to move over the surface of the object while observing the physical condition;

apart from travel over the surface, calibrating the apparatus that senses the physical condition by causing the vehicle to travel over the calibration surface;

detecting a second edge of the object, the step of detecting a second edge of the object being accomplished by a first wheel of the vehicle rolling off the second edge, thereby bringing a slide shoe into contact with the object; and, reversing the direction of travel of the vehicle after detection of the second edge.

2. The method of claim 1 wherein the vehicle is self-propelled.

3. The method of claim 1 wherein the condition of the object being monitored is the physical condition of metallic members within the object.

4. The method of claim 1 wherein the step of calibrating the vehicle is accomplished by traversing the vehicle over a starting block having metallic members imbedded therewithin at predetermined locations.

5. The method of claim 1 wherein the step of sensing the physical condition of the object is accomplished by magnetism.

6. The method of claim 1 wherein a motor powering the vehicle reverses when the first wheel of the vehicle rolls off the first edge of the object.

7. The method of claim 6 wherein, after the motor powering the vehicle reverses, the vehicle traverses back across the object a second distance which is less than a first distance which the vehicle traversed when traversing the width of the object.

8. A method of observing a physical condition of an object at or near a surface of the object utilizing a self-propelled vehicle calibrated with an associated starting block having metallic members embedded therein at predetermined locations, the object having first and second lateral edges, the method comprising the steps of:

positioning the associated starting block adjacent the first lateral edge so that a working surface of the starting block is essentially coplanar with the surface of the object;

calibrating the vehicle by moving it over the working surface;

causing the vehicle to move from the working surface onto the surface of the object, the vehicle traveling in a first direction from the first lateral edge toward the second lateral edge while observing the physical condition;

detecting the second lateral edge of the object; and, reversing the direction of travel of the vehicle after detecting the second edge.

9. The method of claim 8 wherein the vehicle further comprises a first wheel and wherein the step of detecting the second lateral edge includes rolling the first wheel of the vehicle off the second edge.

10. The method of claim 9 further comprising the step of preventing the movement of the vehicle in the first direction following the step of detecting the second lateral edge.

11. The method of claim 8 wherein the step of reversing the direction of travel of the vehicle includes causing the vehicle to move a shorter distance in the reverse direction than the distance the vehicle traveled in the first direction.

* * * * *